(12) United States Patent
Khalaj

(10) Patent No.: US 11,260,179 B2
(45) Date of Patent: Mar. 1, 2022

(54) MULTI-FUNCTIONAL SYRINGE PLUNGER AND METHOD OF USE

(71) Applicant: Ben M. Khalaj, Irvine, CA (US)

(72) Inventor: Ben M. Khalaj, Irvine, CA (US)

(73) Assignee: Ben M. Khalaj, Irvine, CA (US)

( * ) Notice: Subject to any disclaimer, the term of this patent is extended or adjusted under 35 U.S.C. 154(b) by 8 days.

(21) Appl. No.: 16/407,656

(22) Filed: May 9, 2019

(65) Prior Publication Data
US 2020/0353172 A1 Nov. 12, 2020

(51) Int. Cl.
*A61M 5/315* (2006.01)
*A61M 5/31* (2006.01)

(52) U.S. Cl.
CPC ........ *A61M 5/3134* (2013.01); *A61M 5/3135* (2013.01); *A61M 5/3137* (2013.01); *A61M 2005/3131* (2013.01); *A61M 2202/08* (2013.01)

(58) Field of Classification Search
CPC .............. A61M 5/3134; A61M 5/3135; A61M 5/3137; A61M 2005/3131; A61M 2202/08; A61M 2005/31508; A61M 5/31578; A61M 5/31595; A61M 5/315; A61M 5/31511; A61M 5/31513; A61M 5/31515; A61M 5/31576
See application file for complete search history.

(56) References Cited

U.S. PATENT DOCUMENTS

| | | | |
|---|---|---|---|
| 2011/0137246 A1* | 6/2011 | Cali | A61M 5/3234 604/110 |
| 2015/0209521 A1* | 7/2015 | Titus | A61M 5/31511 604/218 |
| 2017/0182254 A1* | 6/2017 | Heinsbergen | A61M 5/31511 |
| 2018/0043102 A1* | 2/2018 | Cojocariu | A61M 5/31513 |

* cited by examiner

*Primary Examiner* — Rebecca E Eisenberg

(57) ABSTRACT

A fat-harvesting syringe having a multi-functional plunger assembly. The plunger assembly comprises an outer plunger rod body, an inner central plunger rod and a piston seal assembly. The outer plunger rod body having a first and a second end. The first end having a central lumen all at its finger grip handle and at the second end having flanges that are expandable. Once the central plunger inner rod is inserted fully into central lumen of plunger rod body, the expandable flanges expands and engages with the piston seal assembly. Also when the inner plunger rod is retracted, the plunger body flanges retract back and disengages from piston seal assembly.

1 Claim, 8 Drawing Sheets

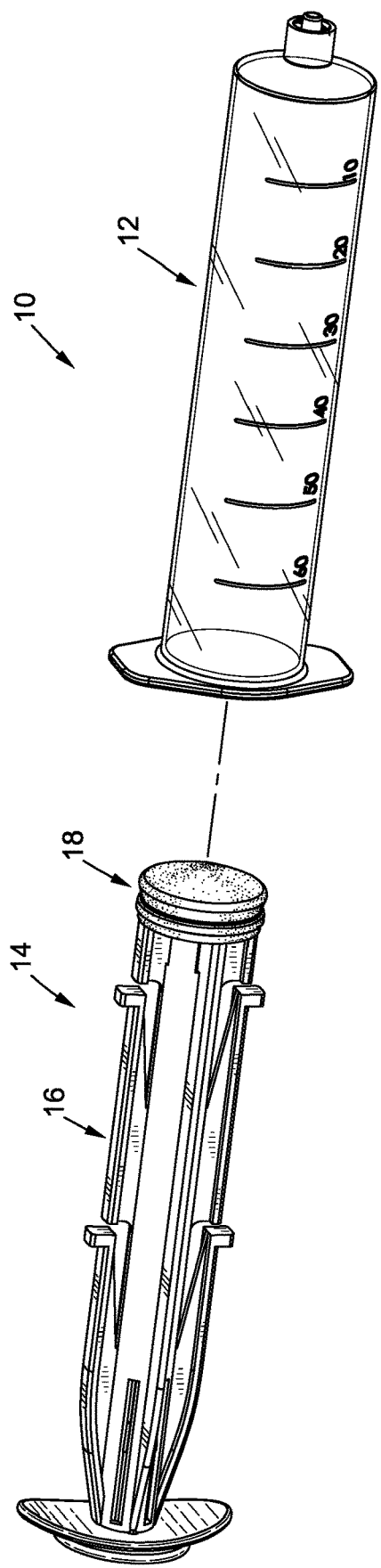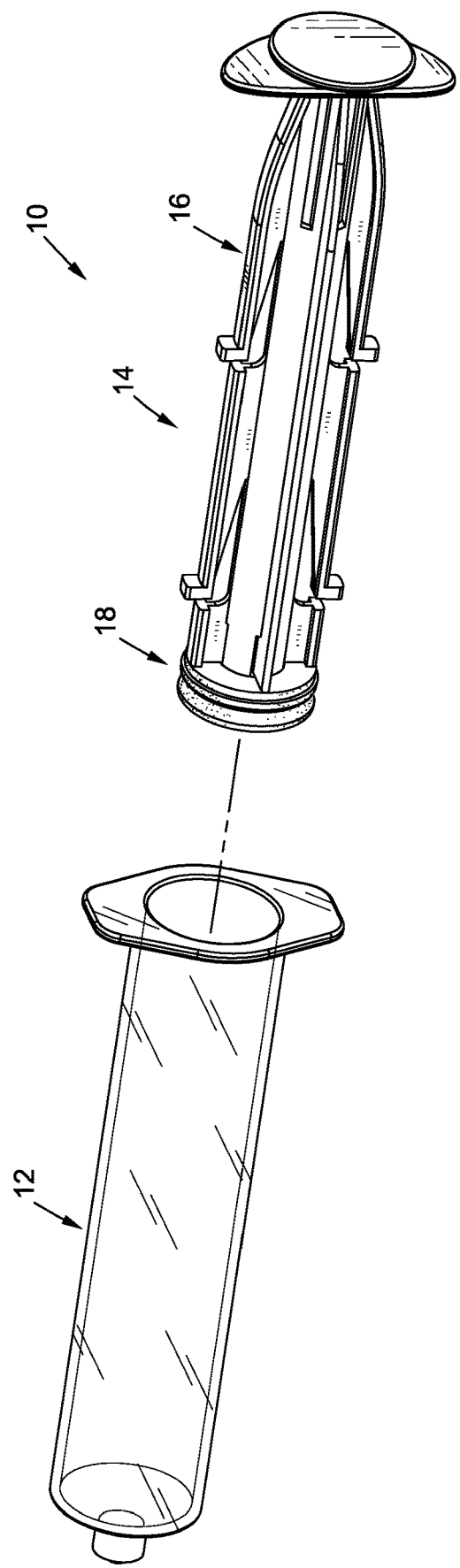
FIG. 1
FIG. 2

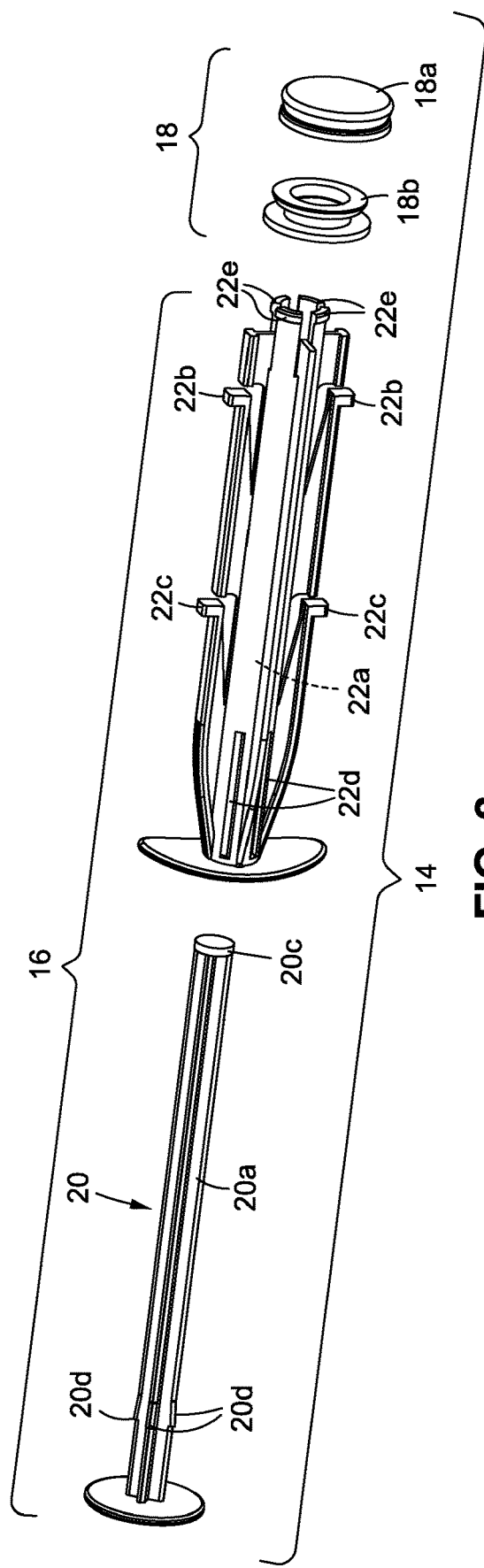
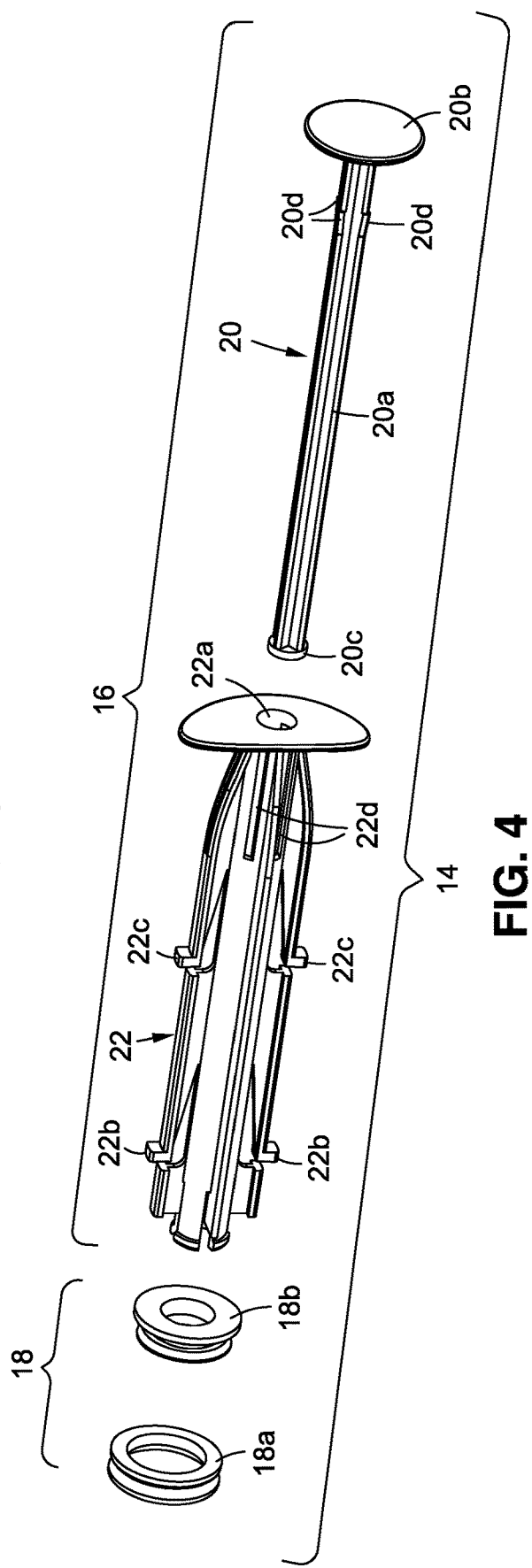

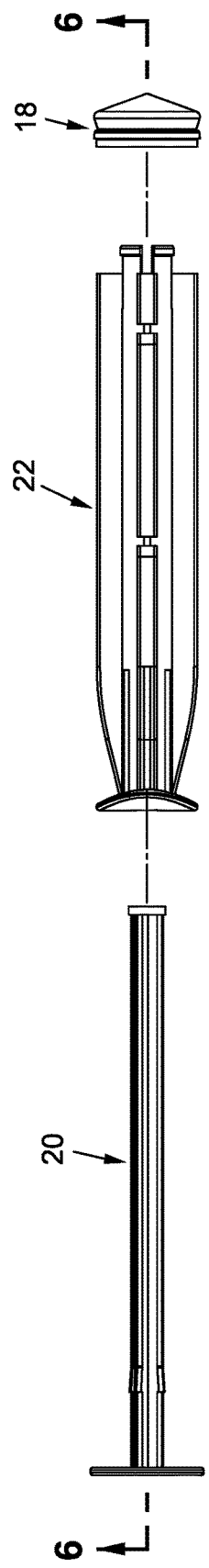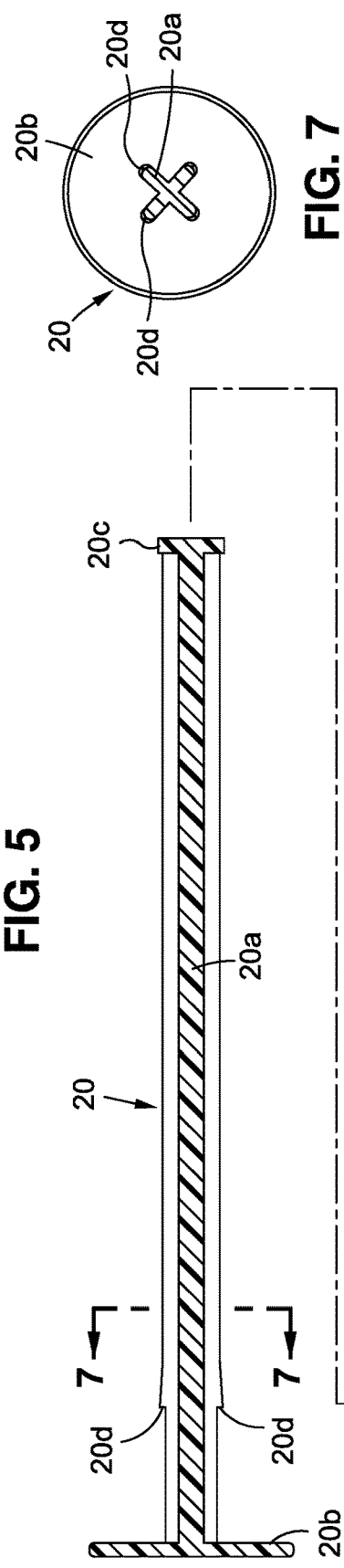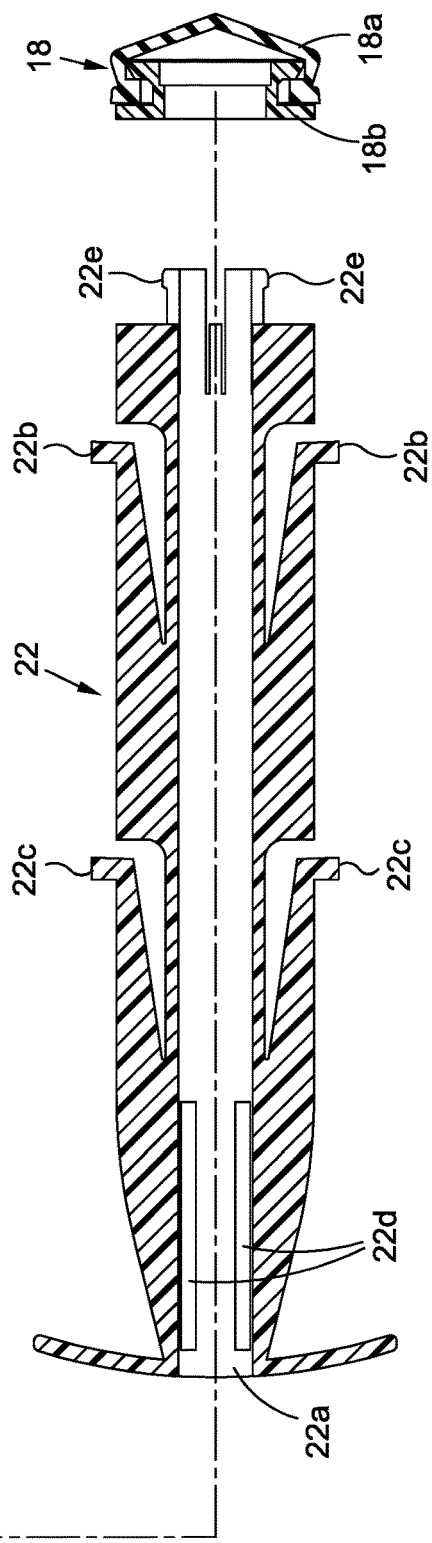
FIG. 5
FIG. 7
FIG. 6

US 11,260,179 B2

MULTI-FUNCTIONAL SYRINGE PLUNGER AND METHOD OF USE

FIELD OF THE INVENTION

The present invention relates to a medical syringe with a plunger to be used in surgery. More particularly the syringe uses a multi-functional plunger for fat-harvesting procedures.

BACKGROUND OF THE INVENTION

Fat-harvesting syringes are used in many liposuction surgical procedures for fat transferring and fat grafting. Typically, a liposuction cannula directly transfers extracted fat cells from a patient to a collection canister or collection syringe barrel with a lure lock system. The syringe plays an important role in fat transferring and fat grafting.

In fat transfer procedures, after the fat cells are extracted from patient and collected in the syringe barrel, the fat cells goes through other important processes such as cell cultivation, separation of fat/stem cells, and conditioning. For these important steps, the surgeon may use separate test tubes to process the fat cells. It is important that the extracted fat cells remain in the same original syringe barrel in a closed loop system, rather than transferring it back and forth into different locations for cell conditioning. Some advantages are faster processing and the elimination of potential contaminates.

To achieve the aforementioned tasks, a syringe should have a plunger assembly that can easily withdraw fat cells, quickly detach and re-attach to a seal assembly for conditioning of the cells, and incrementally re-inject conditioned fat cells back to the patient.

In prior art syringe apparatus, there are plungers that can detach and re-attach using screw type fastener, but it neither has a quick release feature nor can re-inject incrementally.

However, this invention overcomes the shortcomings of prior art and alleviates problems associated with fat-harvesting syringes and other related surgical procedures.

SUMMARY OF THE INVENTION

A fat-harvesting syringe having a multi-functional plunger assembly. The plunger assembly comprises an outer plunger rod body, an inner central plunger rod and a piston seal assembly. The outer plunger rod body having a first and a second end. The first end having a central lumen all at its finger grip handle and at the second end having flanges that are expandable. Once the central plunger inner rod is inserted fully into central lumen of plunger rod body, the expandable flanges expands and engages with the piston seal assembly. Also when the inner plunger rod is retracted, the plunger body flanges retract back and disengages from piston seal assembly. Therefore the surgeon have an option to leave the seal assembly within the syringe barrel for fat cell processing or reconnect the plunger rod body for further injection or withdrawal.

Furthermore, the piston seal assembly having an annular ring and a piston rubber seal The annular ring is rigid made of polymer material and having first end and second end. the first end having circular opening for nesting and mating with the expandable flanges of the plunger rod body for engaging and disengaging the piston seal assembly from the plunger body. The said second end covered by piston seal.

It is also an object of this invention to have a syringe plunger that has plurality of flexible flaps/stopper feature. These stoppers can stop an injection at a preselected dose, or the flaps can be pressed by fingers for plunger advancement into syringe barrel on preselected dose re-injection. The preselected dose injection can be done incrementally.

Further objects and advantages of this invention will become apparent from consideration of the drawings and descriptions that follow.

BRIEF DESCRIPTION OF THE DRAWINGS

The drawings constitute a part of this specification and include exemplary embodiments to the invention, which may be portrayed in various forms. It is to be understood that in some instances various aspects of the invention may be exaggerated or enlarged to facilitate an understanding of the invention.

FIG. 1 is a front perspective view of a fat-harvesting syringe showing the present invention of preferred embodiment with 60 ml dose scale.

FIG. 2 is a rear perspective view of the syringe as shown in FIG. 1.

FIG. 3 is an exploded view of plunger assembly for fat harvesting syringe.

FIG. 4 is an exploded view of plunger assembly similar to FIG. 3 but showing at a different angle.

FIG. 5 is a top plan view of FIG. 3.

FIG. 6 is an exploded cross sectional view taken along line 6-6 in FIG. 5.

FIG. 7 is a cross sectional view taken along line 7-7 in FIG. 6.

DETAILED DESCRIPTION OF THE INVENTION

Figure 8:
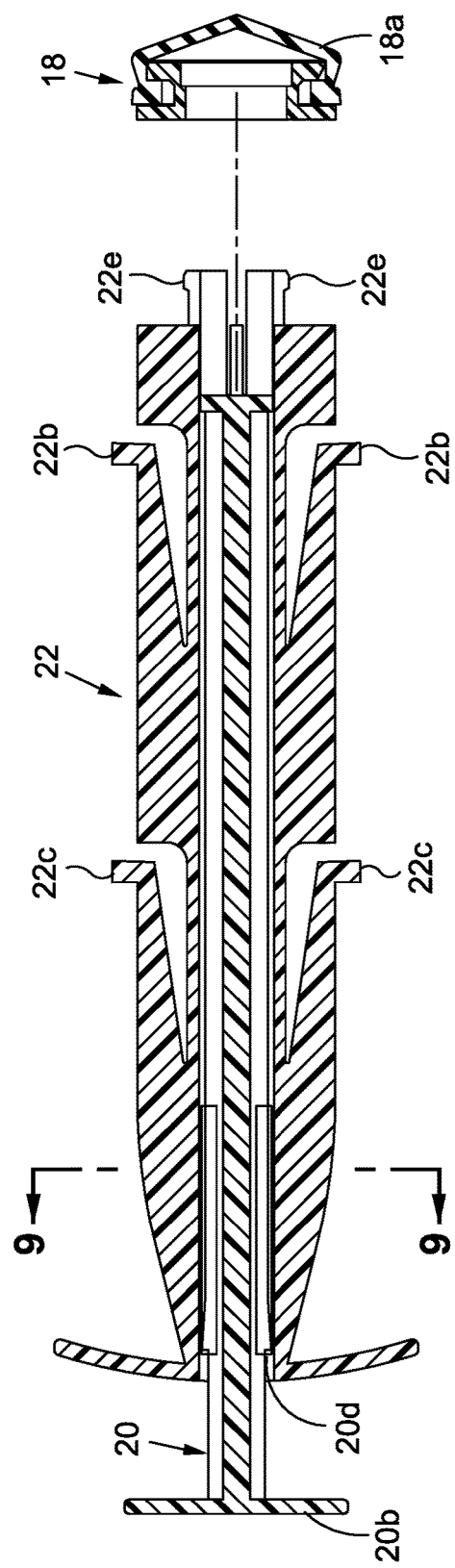
FIG. 8 is a cross sectional view similar to FIG. 6, but the plunger and seal assembly are shown in an detached position.
Figure 9:
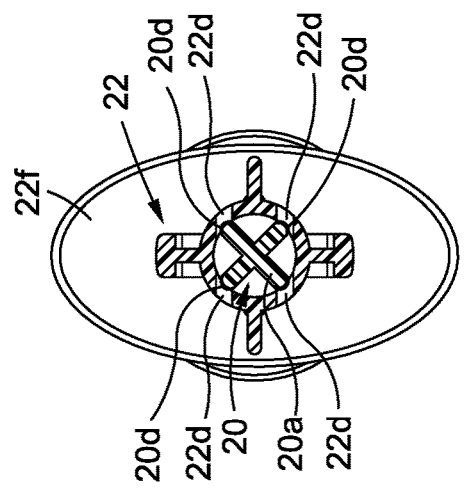
FIG. 9 is a cross sectional view taken along line 9-9 in FIG. 8.
Figure 10:
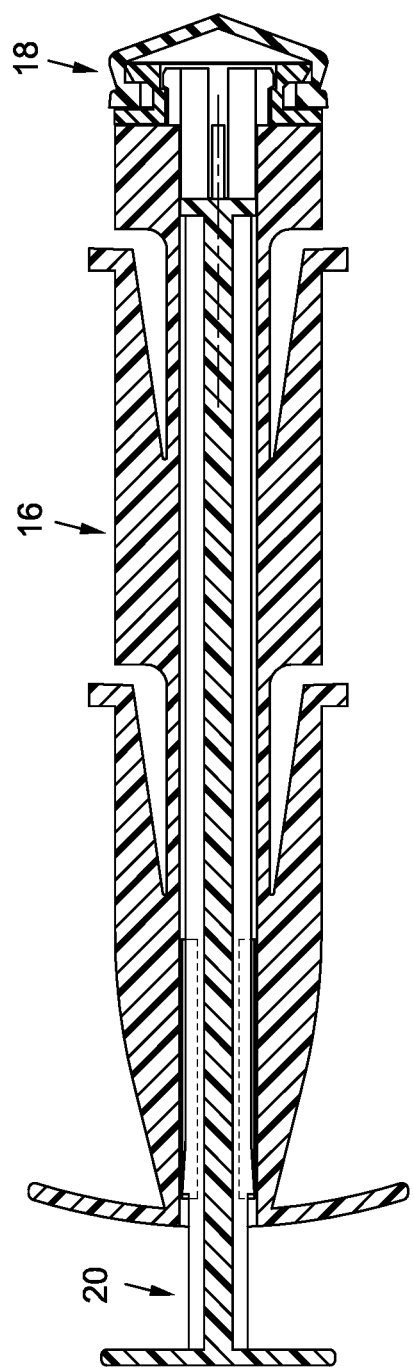
FIG. 10 is a cross sectional view similar to FIG. 8, but the plunger and seal sub-assembly are shown in an unlock deployed position.
Figure 11:
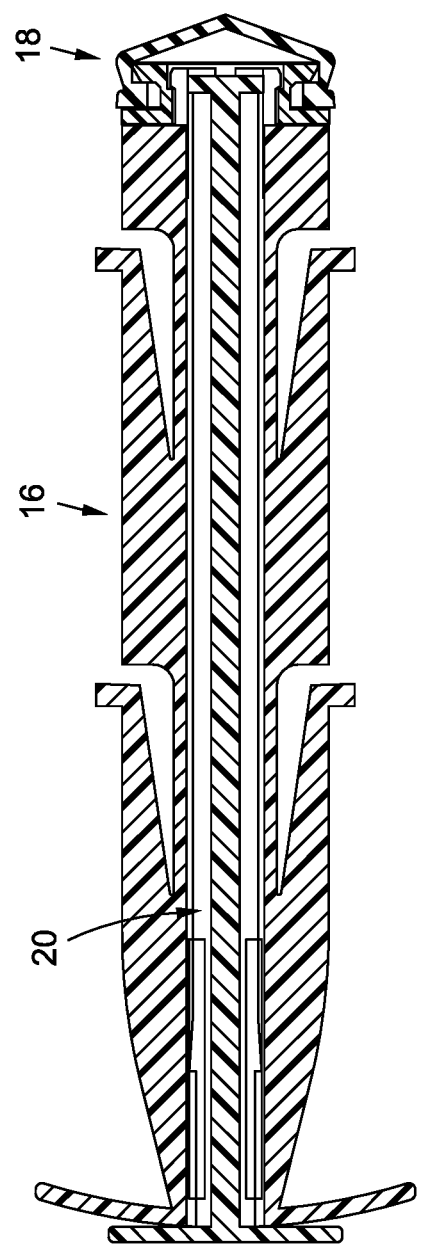
FIG. 11 is a cross sectional view similar to FIG. 10, but the plunger and seal assembly are shown in locked position.
Figure 12:
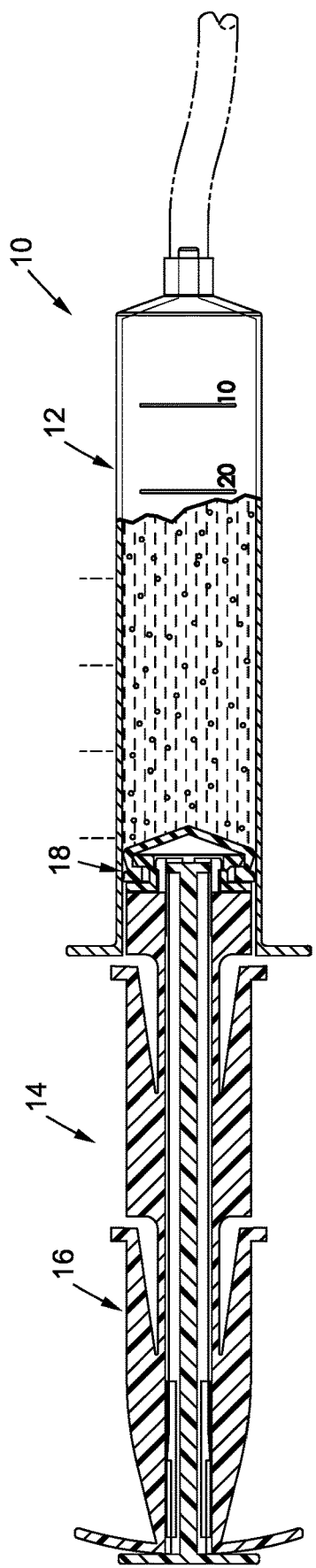
FIG. 12 is a partial cross sectional view shows the plunger and seal assembly inserted into syringe barrel.
Figure 13:
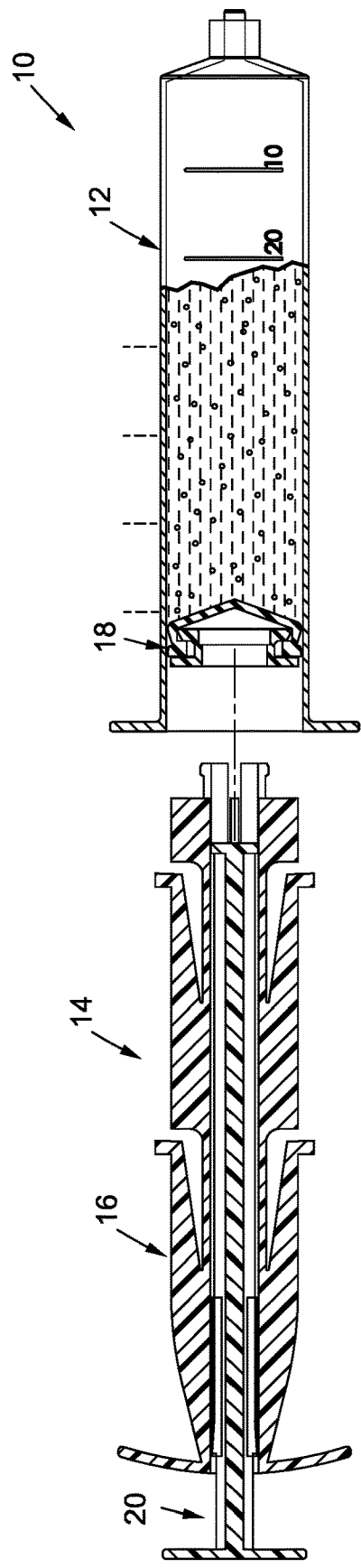
FIG. 13 is a similar view as FIG. 12, but shows the plunger sub-assembly is detached and released from the seal sub-assembly.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

FIG. 1-2 illustrates a preferred embodiment of fat-harvesting syringe 10 having 60 ml dose scale. The syringe apparatus 10 comprises a syringe barrel 12 and a plunger assembly 14. The plunger assembly includes a plunger rod assembly 16 and a piston seal assembly 18. The syringe plunger assembly 14 is a multi-functional plunger that can be attached/detached to the piston seal assembly 16 via a quick connect/disconnect feature.

Now referring to FIG. 3-7, the plunger assembly 14 is shown in exploded view which includes a central inner rod 20, outer body rod 22, and piston seal assembly 18. When the inner rod 20 is centrally inserted into outer body 22 via central lumen 22a, the inner rod 20 slide into outer body rod which has limited linear travel movement due to the plurality of one way barbs 20d on shaft 20a. The travel displacement of the inner rod is limited due to apertures 22d.

At the frontal tip of the plunger outer body rod 22, there are a set of flexible and expandable flanges 22e that can be easily engage or disengage to a piston seal assembly 18. In order to engage the plunger rod assembly 16 to the piston seal assembly 18, the expandable flanges 22e passes through the central opening of the piston seal annular ring 18b and positions itself to overlap inside the annular ring. By sliding the plunger inner rod 20 and its annular frontal tip 20c forward in the plunger outer central lumen 22a, it forces the flanges to radially push back and lock inside the piston seal assembly 18 as best seen in FIG. 8-13. For quickly disconnecting and/or unlocking the plunger rod sub-assembly 16 from the piston seal assembly 18, simply pull the plunger inner rod 20 backward and the flanges 22e disengages from the piston seal assembly 18.

Figure 14:
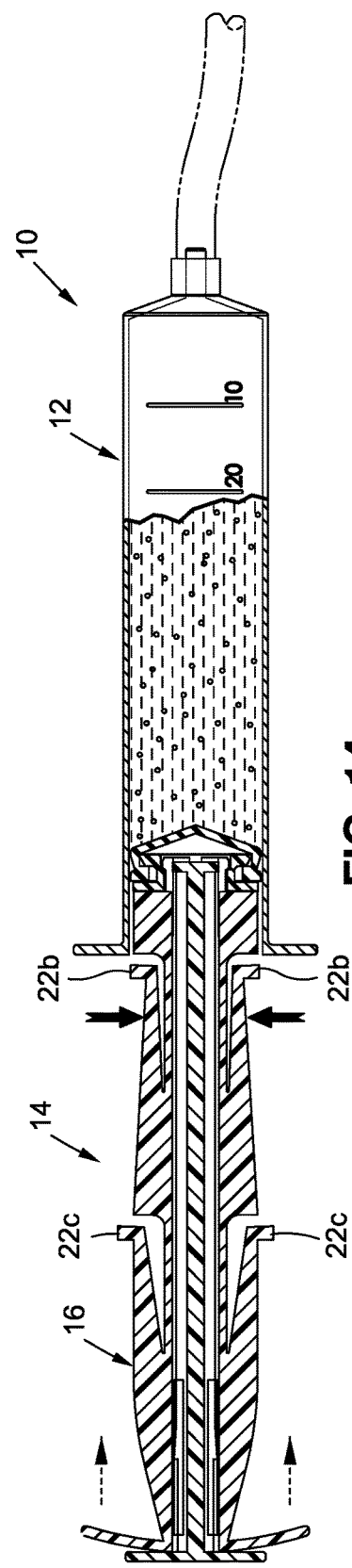
FIG. 14 is a similar view as FIG. 12, but shows that the increment advancement flaps/stopper on the plunger body is pressed in order to make the first increment advancement within the syringe barrel.
Figure 15:
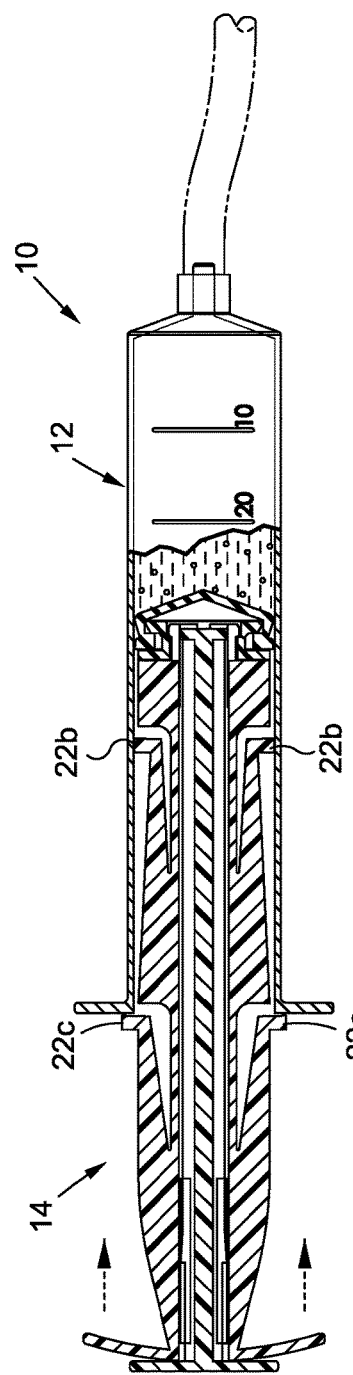
FIG. 15 is a similar view as FIG. 14, but shows the plunger assembly is pushed inside the syringe barrel for the first increment advancement.
Figure 16:
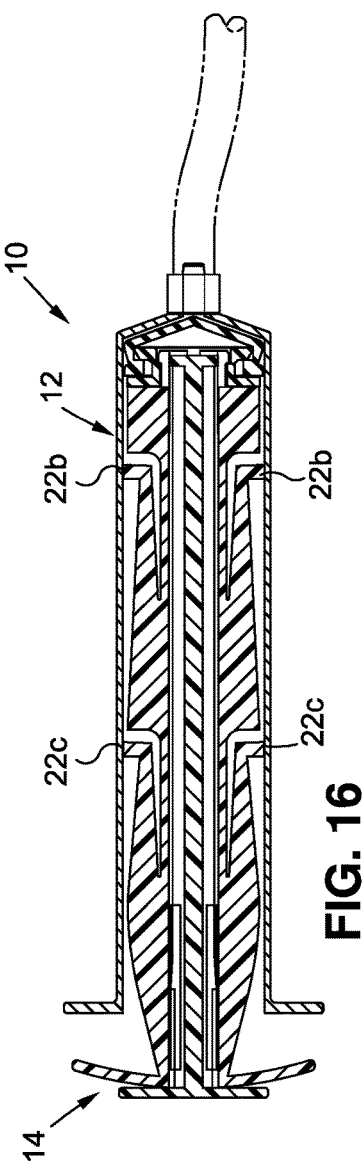
FIG. 16 is a similar view as FIG. 15 but showing the plunger assembly is pushed inside syringe barrel for second increment advancement.

FIG. 14-16 illustrate the plunger rod assembly 16 using flexible flaps stoppers for the purposes of a preset dose stopping or preselected dose re-injection. When flaps 22b are in normal state, the plunger rod assembly 16 cannot advance any further in syringe barrel 12. The flexible flaps are slightly oversized with respect to the syringe barrel opening. However, when these flexible flaps are pressed inward, the plunger rod assembly can advanced into syringe barrel until the next flaps 22c hit the syringe barrel end.

Figure 17:
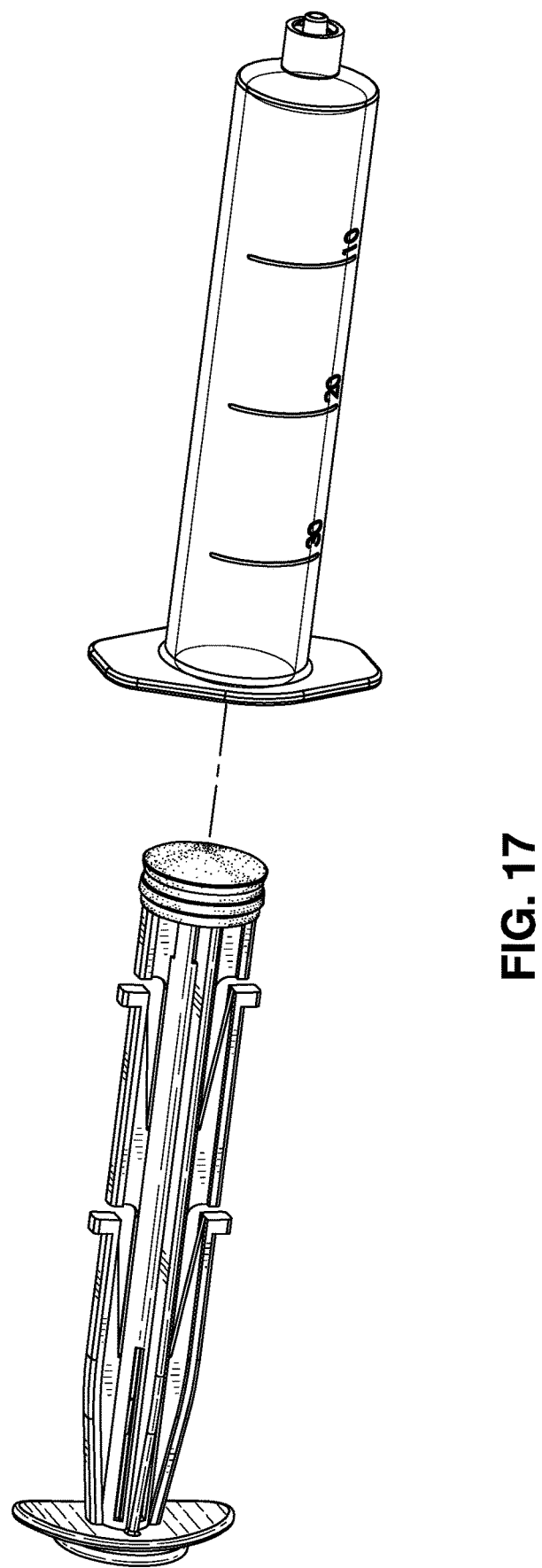
FIG. 17 is a front perspective view of a second embodiment of a fat-harvesting syringe showing smaller version with 30 ml dose scale.

The current preset increments dose scale for plunger rod assembly 16 for each pair of flaps are set at 30 ml increments with respect to a syringe barrel of 60 ml dose scale. However the increments can be modified per syringe size and design. In FIG. 17, the syringe 100 is smaller in size and has a dose scale of 30 ml dose scale.

While this invention is susceptible to embodiments in many different forms, this specification and the accompanying drawings disclose only some specific forms as examples of the invention. The invention is not intended to be limited to the embodiments as described; however, the scope of the invention is pointed out in the appended claims.

I claim:

1. A plunger assembly for a syringe comprising:
    an outer plunger rod body having a first and a second end; with a finger grip handle and a tip; said first end having a central lumen, and the second end said tip having expandable flanges;
    a slideable central plunger inner rod having a first end and a second end; said first end having a finger grip and the second end having a circular solid tip to be engaged with said expandable flanges once the central plunger inner rod is inserted fully into said central lumen of the outer plunger rod body; said outer plunger rod body further includes flexible stoppers at multiple locations for incremental advancement into a syringe barrel, and;
    a piston seal assembly having an annular ring and a piston rubber seal; said annular ring is rigid and having a first end and a second end; said first end having a circular opening for nesting and mating with said expandable flanges of said plunger outer rod body for engaging and disengaging the piston seal assembly from said outer plunger rod body; and said second end of annular ring is covered by the piston rubber seal.

\* \* \* \* \*